United States Patent [19]

Crooker et al.

[11] Patent Number: 6,059,933
[45] Date of Patent: May 9, 2000

[54] INHIBITION OF 141B DECOMPOSITION

[75] Inventors: Richard M. Crooker, Lehigh; Maher Y. Elsheikh, Tredyffrin, both of Pa.; Anthony D. Kelton, Graves; Morris P. Walker, Marshall, both of Ky.; Danny W. Wright, Owatonna, Minn.

[73] Assignee: ELF Atochem North America, Inc., Philadelphia, Pa.

[21] Appl. No.: 08/428,709

[22] Filed: Apr. 25, 1995

Related U.S. Application Data

[63] Continuation of application No. 08/119,905, Sep. 10, 1993, Pat. No. 5,531,867, which is a continuation of application No. 07/983,919, Dec. 1, 1992, abandoned, which is a continuation-in-part of application No. 07/869,225, Apr. 14, 1992, abandoned.

[51] Int. Cl.$^7$ .......................... B01D 3/34; C07C 17/386
[52] U.S. Cl. .................. 203/6; 203/58; 203/59; 203/68; 570/178
[58] Field of Search ............... 203/6–9, 2, 62–65, 203/86, 57, 58–59, 68–70; 570/111, 102, 177, 175, 122, 178

[56] References Cited

U.S. PATENT DOCUMENTS

| | | |
|---|---|---|
| 2,831,902 | 4/1958 | Hamilton et al. . |
| 3,142,708 | 7/1964 | Young . |
| 3,689,373 | 9/1972 | Hutchinson . |
| 3,763,017 | 10/1973 | Yves et al. . |
| 4,178,316 | 12/1979 | Schultz et al. . |
| 4,422,913 | 12/1983 | Larsen et al. . |
| 4,548,701 | 10/1985 | Wolff . |
| 4,766,261 | 8/1988 | Bierl . |
| 4,948,479 | 8/1990 | Brooks et al. . |
| 4,954,330 | 9/1990 | Ziegenhain . |
| 4,960,580 | 10/1990 | Gumprecht . |
| 4,968,850 | 11/1990 | Franklin et al. . |
| 4,973,774 | 11/1990 | Rozen et al. . |
| 4,975,156 | 12/1990 | Wismer . |
| 5,001,287 | 3/1991 | Fernandez et al. . |
| 5,105,035 | 4/1992 | Wang et al. . |
| 5,118,438 | 6/1992 | Magid et al. ............... 203/67 |
| 5,120,461 | 6/1992 | Logsdon et al. . |
| 5,122,294 | 6/1992 | Logsdon et al. . |
| 5,126,067 | 6/1992 | Swan et al. . |
| 5,135,680 | 8/1992 | Crooker et al. . |
| 5,169,995 | 12/1992 | Crooker et al. ............... 570/111 |
| 5,200,431 | 4/1993 | Dattani et al. . |
| 5,306,850 | 4/1994 | Darago . |

FOREIGN PATENT DOCUMENTS

| | | |
|---|---|---|
| 0 472 391 A1 | 2/1992 | European Pat. Off. . |
| 0046804 | 12/1978 | Japan . |
| 64-50829 | 2/1989 | Japan . |
| 64-56630 | 3/1989 | Japan . |
| 63-91608 | 10/1989 | Japan . |
| 2215738 | 8/1990 | Japan . |
| 4-297427 | 10/1992 | Japan . |

*Primary Examiner*—Virginia Manoharan
*Attorney, Agent, or Firm*—Finnegan, Henderson, Farabow, Garrett & Dunner, L.L.P.

[57] ABSTRACT

Inhibition of the formation of unsaturated carbon compounds during the heating of 141*b* involving the addition of various inhibitors such as butylene oxide and/or the use of a vessel made of a nickel alloy.

22 Claims, No Drawings

INHIBITION OF 141B DECOMPOSITION

CROSS-REFERENCE TO RELATED APPLICATION

This is a continuation of application Ser. No. 08/119,905, filed Sept. 10, 1993, now U.S. Pat. No. 5,531,867, which was a continuation of application Ser. No. 07/983,919, filed Dec. 1, 1992, abandoned, which was a continuation-in-part of application Ser. No. 07/869,225, filed Apr. 14, 1992, abandoned.

FIELD OF THE INVENTION

The present invention relates to a method of inhibiting the formation of unsaturated carbon compounds and other unwanted by-products formed during the heating of 1,1-dichloro-1-fluoroethane ("141b"), especially as it relates to the separation of 141b from a liquid mixture containing 1,1,1,2-tetrachloroethane ("130a") and, if present, 1,1,1-trichloroethane ("140a") via distillation.

BACKGROUND OF THE INVENTION

The hydrochlorofluorocarbon 141b is a replacement for trichlorofluoromethane ("11") as a foam blowing agent. As shown by Brooks et al. in U.S. Pat. No. 4,948,479 (the entire specification of which is hereby incorporated by reference), however, the manufacture of 141b from 140a and hydrogen fluoride ("HF") results in the formation of vinylidene chloride ("1130a") and other unsaturated by-products and acids, principally HCl. Because of similar boiling points, 141b (b.p. 32° C.) and 1130a (b.p. 31° C.) cannot be readily separated by distillation. Thus, Brooks et al. teach the use of a photochlorination step to convert the 1130a in the 141b product stream to the higher boiling 130a (b.p. 130.5° C.), then distillation of the photochlorinated liquid mixture to separate the low boiling 141b from the higher boiling liquids such as 130a (and possibly 140a unless it has been removed upstream). However, it is found that 1130a and acid (primarily HCl with lesser amounts of HF) are reformed in the distillation column and distill overhead with the 141b product. While the acid can be removed from the product by selective adsorption or reaction, such as by passing the acidic 141b through a bed of potassium hydroxide, it is undesirable since it is an added step. Reformation of the 1130a is more difficult, however, because as noted above it has nearly the same boiling point as the desired 141b product. Thus, yet another post-treatment would be required to remove the 1130a unless its formation in the distillation column can be inhibited. The same problem is presented when 141b is formed by the reaction of 1130a and HF [as taught, for example, by Henne et al., JACS 65, 1271 (1943)], resulting in a product stream containing 141b and 1130a.

SUMMARY OF THE INVENTION

A method is provided for inhibiting the formation of unsaturated carbon compounds during the heating of 141b (alone or as a liquid mixture containing 130a or both 130a and 140a), which method comprises conducting said heating (a) in the presence of an effective amount of an inhibitor selected from a dialkylhydroxylamine where the alkyl groups have 1 to 4 carbons such as methyl, ethyl, propyl, or butyl [preferably diethylhydroxylamine ("DEHA")]; an epoxide (or cyclic oxide) having 3 to 6 or 10 to 30 carbons such as alpha-pinene oxide ("APO"), 1,2-hexadecene oxide ("HO"), butylene oxide ("BO"), limonene monoxide, limonene dioxide, methyl epoxy soyate, propylene oxide, dicyclopentadiene dioxide alcohol, isoprene oxide, glycidyl isopropyl ether, 1,4-dioxane, or an epoxidized alpha olefin such as $C_{10}H_{20}O$, $C_{12}H_{24}O$, or $C_{16}H_{32}O$ (preferably APO, HO, or BO); a free radical scavenger having at least two double bonds and a boiling point greater than that of 141b such as alpha-methylstyrene ("AMS"), limonene or one of its optical isomers such as d-limonene ("DL"), alloocimene, or isoprene (preferably AMS or DL); a phenol, the phenyl group of which can be unsubstituted or substituted at one or more of the ring positions with substituents separately selected from alkyl (such as methyl, ethyl, isopropyl, butyl), alkoxy (such as methoxy, ethoxy, propoxy, isopropoxy), nitro, halo (such as F, Cl, or Br), alkylamine salt (such as —N(CH$_3$)$_3^+$Cl$^-$), acyl (—C(O)R where R is alkyl), acyloxy (—OC(O)R where R is alkyl), cyano, hydroxy, phenyl which is unsubstituted or substituted as above, the alkyl portion of such substituents generally being lower alkyl of 1 to 4 carbons, and wherein two adjacent positions of the phenyl group can have substituents which are joined to form a fused aromatic ring as in naphthol (preferred phenols being 2,6-di-t-butyl-4-methylphenol and 4-methoxyphenol); or a 1,4-benzoquinone which can be unsubstituted or substituted at each of the aromatic ring positions with substituents separately selected from those listed for phenol (the preferred benzoquinone being unsubstituted); or (b) in a vessel made of a nickel alloy.

This method is particularly applicable to separation of 141b from a liquid mixture containing 130a (and, optionally, 140a) in a distillation column. If an inhibitor is used, it is added to the bottom (or "reboiler" section) of the column. If the column is made of a nickel alloy, use of an inhibitor is not necessary.

DETAILED DESCRIPTION OF THE INVENTION

In one embodiment of the invention it has now been found that the presence of the aforementioned inhibitors inhibits the formation of unsaturated carbon compounds such as 1130a and acids such as HCl and HF during the heating of 141b, such as occurs when a liquid mixture comprising 141b, 130a, and, optionally, 140a is heated in a distillation column to separate low boiling compounds such as 141b from higher boiling compounds such as 130a (and 140a, if present).

When added to a distillation column, the inhibitor should be added to the bottom or reboiler section of the column where the temperature is highest, typically on the order of from about 75° F. to about 200° F. (preferably about 90–160° F.). The temperature at the top of the column is typically about 20 degrees lower than that at the bottom. Adding the inhibitor to the feed stream to the column, as opposed to the column bottom, has been found to be ineffective.

The inhibitor is generally fed to the column at a rate sufficient to maintain a level of inhibitor in the bottoms stream exiting the column of from about 500 to about 5000 ppm, more typically from about 1500 to about 3500 ppm.

This embodiment is illustrated in Examples 1–5 below (where percents are weight percent unless otherwise noted). Examples 1–3 employ a conventional carbon steel column.

In a second embodiment it has now been found that the use of nickel alloys such as Nickel, Monel, Inconel, Hastelloy, or Carpenter 20 for the vessel in which the heating or distillation is conducted is effective to inhibit the formation of acids and 1130a without the use of inhibitors. Inconel and Hastelloy alloys are particularly preferred. Exclusion of air from such processes also assists in the inhibition. This embodiment is illustrated by Example 5 and 6.

EXAMPLE 1

A crude, photochlorinated mixture, produced according to the methods of the Brooks et al. patent and containing about 100 ppm of 1130a and, as the other major components, about 98% 141b, 1.5% 140a, and 0.3% 130a, was distilled in a steam-heated column which was operated at a temperature at the column top of about 120° F., a temperature at the column bottom of about 140° F., and a pressure of about 15 PSIG. The 141b taken overhead typically showed the formation of 300 to 600 ppm of 1130a and over 20 ppm acidity (calculated as HCl).

EXAMPLE 2

Example 1 was repeated except that butylene oxide was fed to reboiler section of the column at a rate sufficient to maintain a level of 2500 ppm of the butylene oxide in the bottoms stream. There was no detectable formation of 1130a or acid as a result of the distillation.

EXAMPLE 3

Examples 1 and 2 were repeated except that the 140a level in the feedstream was reduced to about 50 ppm. Distillation as in Example 1 resulted in the formation of about 170 ppm of 1130a and over 10 ppm acidity. With the use of butylene oxide as in Example 2, distillation resulted in the formation of only about 30 ppm of 1130 and about 1 ppm of acidity.

EXAMPLE 4

A) A mixture containing as major components about 84.1% 141b, 0.2% 130a, and 15.3% 140a was tested to compare the ability of various inhibitors to prevent the formation of acidity (the starting mixture contained 5.3 ppm acid as HCl). Samples containing 2000 ppm of inhibitor (except in the control with no inhibitor) were placed in glass bottles and set one inch from a 450-watt UV lamp for 5 hours. With no inhibitor (the control) over 120 ppm of acidity resulted. With six inhibitors of this invention (DEHA, APO, HO, BO, AMS, and DL) less than 10 ppm of acidity resulted.

B) The above test was repeated except that the samples were placed in mild steel cylinders and heated at 100 degrees Centigrade for 7 hours. With no inhibitor (the control) over 170 ppm of acidity resulted. With nine inhibitors of this invention (DEHA, APO, HO, BO, AMS, DL, benzoquinone, 4-methoxyphenol, and 2,6-di-t-butyl-4-methylphenol) less than 10 ppm of acidity again resulted.

EXAMPLE 5

Crude, 141b-containing, column bottom material was heated in cylinders made of different metals and analyzed. A 316 Stainless Steel container heated to 180° F. for 16.5 hours showed a 5-fold increase in 1130a, while the same container heated to 252° F. for 23 hours showed no increase in 1130a when 1800 ppm of butylene oxide inhibitor was added. Mild steel containers heated to 257° F. for 4 hours showed a 340 ppm increase in 1130a with no inhibitor, but only a 50 ppm increase in 1130a when 1600 ppm of butylene oxide inhibitor was added. When Monel (an alloy containing 63–70% by weight nickel) was heated to 257° F. for 4 hours, no increase in 1130a occurred even though no inhibitor was present.

EXAMPLE 6

Relatively pure 141b samples (99.3% 141b) without inhibitor were placed in glass tubes containing small coupons of various metals and heated for 2 hours at 356° F. The mild and stainless steels resulted in the formation of 495–1755 ppm of 1130a, while Inconel 600 (an alloy containing 72% nickel) and Hastelloy C-276 (an alloy containing about 60% nickel) resulted in no 1130a formation, Nickel (99–100% nickel) resulted in 250 ppm of 1130a, Monel 400 (63–70% nickel) resulting in 335 ppm of 1130a, and Carpenter 20 (an alloy containing 32–38% nickel) resulted in 450 ppm of 1130a.

What is claimed is:

1. A purification process for a hydrofluoroalkane comprising:
   distilling said hydrofluoroalkane to separate therefrom impurities which are less volatile than said hydrofluoroalkane, said distillation performed in the presence of an inhibitor.

2. The process according to claim 1, wherein said inhibitor is an amine, an epoxide having 3 to 6 or 10 to 30 carbons, or an unsaturated hydrocarbon.

3. The process according to claim 1, wherein said inhibitor is a free radical scavenger.

4. The process of claim 2, wherein said epoxide is butylene oxide.

5. The process of claim 2, wherein said unsaturated hydrocarbon is a $C_3$–$C_8$ unsaturated hydrocarbon.

6. A purification process for 1,1-dichloro-1-fluoroethane, comprising:
   distilling said 1,1-dichloro-1-fluoroethane to separate therefrom impurities which are less volatile than said 1,1-dichloro-1-fluoroethane, said distillation performed in the presence of an inhibitor for inhibiting the formation of unsaturated carbon compounds during said distilling.

7. The process according to claim 6, wherein said inhibitor is an amine, an epoxide having 3 to 6 or 10 to 30 carbons, or an unsaturated hydrocarbon.

8. The process according to claim 6, wherein said inhibitor is a free radical scavenger.

9. The process of claim 7, wherein said epoxide is butylene oxide.

10. The process of claim 7, wherein said unsaturated hydrocarbon is a $C_3$–$C_8$ unsaturated hydrocarbon.

11. A method for inhibiting the formation of unsaturated carbon compounds during the distillation of 1,1-dichloro-1-fluoroethane, comprising distilling 1,1-dichloro-1-fluoroethane in the presence of an inhibitor.

12. The method of claim 11, wherein said inhibitor is an amine, an epoxide having 3 to 6 or 10 to 30 carbons, or a free radical scavenger.

13. The process of claim 12, wherein said free radical scavenger is a $C_3$–$C_8$ unsaturated hydrocarbon.

14. The process of claim 12, wherein said epoxide is butylene oxide.

15. In a process for separating 1,1-dichloro-1-fluoroethane from a liquid mixture containing 1,1,1,2-tetrachloroethane in a distillation column, the improvement which comprises feeding butylene oxide to the bottom section of the column at a rate sufficient to maintain from about 500 ppm to about 5000 ppm of butylene oxide in the stream exiting the column bottom and maintaining the bottom of said column at a temperature of from about 90 to about 160 degrees Fahrenheit.

16. A method for inhibiting the formation of unsaturated carbon compounds during the distillation of a hydrofluoroalkane, comprising distilling said hydroflouroalkane in the presence of an inhibitor.

17. The method of claim 16, wherein said inhibitor is an amine, an epoxide having 3 to 6 or 10 to 30 carbons, or a free radical scavenger.

18. The process of claim 17, wherein said free radical scavenger is a $C_3$–$C_8$ unsaturated hydrocarbon.

19. The process of claim 17, wherein said epoxide is butylene oxide.

20. A method of heating of 1,1-dichloro-1-fluoroethane, which method comprises heating 1,1-dichloro-1-fluoroethane in the presence an inhibitor which is butylene oxide for inhibiting the formation of vinylidene chloride during said heating.

21. In a process for separating 1,1-dichloro-1-fluoroethane from a liquid mixture containing 1,1,1,2-tetrachloroethane in a distillation column, the improvement which comprises adding to the bottom section of said column, an inhibitor which is butylene oxide for inhibiting the formation of vinylidene chloride during said separating.

22. A process as in claim 21, wherein the bottom of said column is maintained at a temperature of from about 90 to about 160 degrees Fahrenheit.

* * * * *

UNITED STATES PATENT AND TRADEMARK OFFICE
CERTIFICATE OF CORRECTION

PATENT NO.: 6,059,933

DATED: May 9, 2000

INVENTOR(S): Richard M. CROOKER, Maher Y. ELSHEIKH, Anthony D. KELTON, Morris P. WALKER, Danny W. WRIGHT It is certified that an error appears in the above-identified patent and that said Letters Patent is hereby corrected as shown below:

Claim 20, col. 5, last line after "presence" insert --of--.

Claim 21, col. 6, line 6, before "which" insert --of--.

Signed and Sealed this

Twentieth Day of March, 2001

*Attest:*

NICHOLAS P. GODICI

*Attesting Officer*     *Acting Director of the United States Patent and Trademark Office*